United States Patent [19]

Boehning et al.

[11] Patent Number: 4,740,493
[45] Date of Patent: Apr. 26, 1988

[54] SILVER CATALYST AND ITS PREPARATION

[75] Inventors: Karl-Heinz Boehning, Darmstadt; Wolf D. Mross, Frankenthal; Matthias Schwarzmann, Limburgerhof; Hans-Juergen Becker, Neustadt; Juergen Plueckhan; Klaus-Christian Renner, both of Frankenthal, all of Fed. Rep. of Germany

[73] Assignee: BASF Aktiengesellschaft, Ludwigshafen, Fed. Rep. of Germany

[21] Appl. No.: 889,499

[22] Filed: Jul. 25, 1986

[30] Foreign Application Priority Data

Aug. 7, 1985 [DE] Fed. Rep. of Germany ....... 3528313

[51] Int. Cl.$^4$ .......................... B01J 21/04; B01J 23/50
[52] U.S. Cl. ...................................... 502/348; 549/534
[58] Field of Search ............................... 502/347, 348

[56] References Cited

U.S. PATENT DOCUMENTS

| | | | |
|---|---|---|---|
| 2,294,383 | 9/1942 | Carter | 260/348 |
| 3,172,893 | 3/1965 | Ameen | 260/348.5 |
| 3,423,328 | 1/1969 | Keith et al. | 252/430 |
| 3,962,136 | 6/1976 | Nielsen et al. | 252/454 |
| 4,010,115 | 3/1977 | Nielsen et al. | 502/348 X |
| 4,455,392 | 6/1984 | Warner et al. | 502/347 |
| 4,458,032 | 7/1984 | Rebsdat et al. | 502/348 |

*Primary Examiner*—W. J. Shine
*Attorney, Agent, or Firm*—Keil & Weinkauf

[57] ABSTRACT

A silver catalyst for the direct oxidation of ethylene with oxygen to give ethylene oxide is applied on a porous carrier and essentially consists of α-alumina and contains certain amounts of soluble calcium, aluminum, potassium and sodium salts. The carrier has a BET surface area of from 0.2 to 0.8 m$^2$/g, a pore volume of not less than 0.5 ml/g, the pores being equally accessible to cold and warm water, and a bulk density of less than 650 kg/m$^3$, and has a shape which, in the reactor, provides a geometric surface area of not less than 600 m$^2$/m$^3$, on which more than 13% by weight of silver are applied as the active component, more than 110 kg of silver being available per m$^3$ of reactor.

5 Claims, No Drawings

SILVER CATALYST AND ITS PREPARATION

It is known that silver-containing catalysts can be used for the direct oxidation of ethylene with oxygen to give ethylene oxide. α-Alumina is generally used as the carrier for the preparation of the silver catalysts. Various processes for applying the catalytically active component, silver, onto the carrier have been disclosed (U.S. Pat. Nos. 2,294,383, 3,423,328 and 3,172,893).

The literature contains discrepancies with regard to desirable properties for the carrier. As a rule, very wide ranges of physical properties of the carrier are claimed in patents.

For example, German Laid-Open Application No. DOS 3,010,533 states specific surface areas of less than 1 m$^2$/g and pore volumes of from 0.2 to 0.6 cm$^3$/g, with a pore diameter of from 500 to 50,000 nm. The chemical composition of the carrier is said not to be critical. 700 kg/m$^3$ is stated as a possible bulk density.

German Laid-Open Application No. DOS 2,712,785 describes carriers having BET surface areas of 0.03 to 2 m$^2$/g and pore volumes of from 0.25 to 0.65 cm$^3$/g as being particularly useful. Similar statements appear in U.S. Pat. No. 3,962,136.

In contrast, very recent industrial experience has shown that only small sections of the known ranges give truly advantageous properties for the catalysts prepared. Surprisingly good results in terms of activity, selectivity and especially catalyst life are obtained from the direct oxidation of ethylene with oxygen to give ethylene oxide, using a silver catalyst on a porous carrier consisting of α-alumina which contains a certain amount of soluble calcium, aluminum, potassium and sodium salts, has a BET surface area of from 0.2 to 0.8 m$^2$/g, a pore volume of not less than 0.5 ml/g, the pores being equally accessible to cold and warm water, and a bulk density of less than 650 kg/m$^3$, and has a shape which, in the reactor, provides a geometric surface of not less than 600 m$^2$/m$^3$, on which more than 13% by weight of silver are applied as the active component, more than 110 kg of silver being available per m$^3$ of reactor.

The carrier which is important for the activity of the catalysts is prepared from alumina and should contain not less than 99% by weight of α-Al$_2$O$_3$. The content of ionic calcium and/or aluminum compounds which are soluble in nitric acid can be from 200 to 2,000 ppm, and the contents of soluble potassium and/or sodium compounds should not fall below 50 ppm. The carrier of very pure α-Al$_2$O$_3$ should advantageously have a BET surface area of not less than 0.3 m$^2$/g and not more than 0.7 m$^2$/g. The pore volume of the carrier is advantageously determined by the generally known method of water absorption or mercury porosimetry. The pore volume determined by exposure to water at room temperature for five minutes should not differ substantially, eg. by no more than 10%, from the volume determined by the stated methods.

The pore distribution is bimodal, the larger pores preferably accounting for not less than 50% of the total pore volume and having a mean diameter of from about 10,000 to 40,000 nm, and the smaller pores having a diameter of from about 500 to 2,000 nm. By choosing suitable geometric shapes for the carrier particles, the bulk density of the carrier can be adjusted so that it does not exceed 650 kg/m$^3$ and the external geometric surface area of the catalyst per reactor volume does not fall below 600 m$^2$/m$^3$.

The catalytically active metal components are applied by an impregnation method which may consist of one or more impregnation stages and comprises one or more heating stages. During this procedure, not less than 13% by weight of silver should be deposited on the catalyst carrier, and the amount of silver should reach not less than 110 kg per m$^3$ of reactor.

The novel silver catalysts are used for the preparation of ethylene oxide from ethylene and oxygen in the gas phase. The advantage is that, when used for the preparation of ethylene oxide, these catalysts exhibit a decrease in selectivity which is only half as large as that shown by the conventional catalysts, and the lives are accordingly substantially longer. At the same time, the catalysts are more flexible in terms of space velocity.

EXAMPLES, CATALYST PREPARATION

The catalysts according to the invention and the conventional catalysts on the various carriers are prepared by the following general procedure:

Silver nitrate is dissolved in twice the molar amount of sec-butylamine. 2 ml of an aqueous lithium nitrate solution (22.75 g of LiNO$_3$ per 100 ml of solution) are added to this solution, per batch, for 100 g of carrier. The volume of the solution is then increased by 10% by adding deionized water. The carrier is impregnated with the solution according to the expected absorption of liquid by the carrier, and is stored at room temperature for one day. Thereafter, the impregnated carrier is transferred to a through-circulation oven and heated at 240° C. in a stream of nitrogen until the reaction has died down.

In a second impregnation step, the catalyst is treated with an amount of a methanolic solution which is sufficient to effect complete impregnation and contains 1% by volume of sec-butylamine and 0.3 ml of a cesium hydroxide solution (5.46 g of CsOH per 100 ml of solution in methanol). This is followed by a drying step, carried out in a stream of nitrogen.

USE EXAMPLE 1

The abovementioned catalysts are comminuted, and in each case 10 g of the sieve fraction 0.6 to 0.75 mm are introduced into a stainless steel reactor having an internal diameter of 5 mm. The reactor possesses a jacket through which a thermostatting liquid is passed. A gas composed of 30% of ethylene, 8% of oxygen and 2 ppm of inhibitor, the remainder being nitrogen, is passed through the reactor. The pressure is 16 bar and the space velocity is 3,300 l (S.T.P.) of gas per l of catalyst per hour. The temperature is controlled so that the conversion based on oxygen is 50%. After 2 days, samples are taken and the activity and selectivity are determined.

The advantageous reaction results which can be obtained using the catalysts prepared on carriers A and B are summarized in Table 3 and are the average values for various measurements. The less advantageous results obtained with all other carriers (C-I) are shown in the second part of the Table.

USE EXAMPLE 2

Catalysts A, B, C, F and I are introduced, without being comminuted and in an amount of 13 dm$^3$ in each case, into a steel pressure-tight tube reactor corresponding to the single tube conventionally employed in industrial plants. The reactor possesses a jacket through which a thermostatting liquid is passed. A gas which is roughly composed of 30% of ethylene, 8% of oxygen, 6.5% of $CO_2$, 4% of argon, 3 ppm of inhibitor and 50% of methane is passed through the reactor. The pressure is 16 bar. In a first test series, the temperature in the cooling medium of the reactor is adjusted so that a conversion based on oxygen of 35% is achieved at a space velocity of 2,000 m$^3$ (S.T.P.) of gas per m$^3$ of catalyst per hour. In a second test series, 50% of the oxygen is converted at a space velocity of 4,000 m$^3$ (S.T.P.) of gas per m$^3$ of catalyst per hour. Samples are taken after one month and after 12 months.

Table 4 shows the life characteristics and flexibility of space velocity for the catalysts used.

The novel carriers have the properties summarized in Table 1 below. Similar known carriers which possess properties which differ in various respects are shown in Table 2. These carriers do not have the desired advantageous properties, as shown in the Examples below.

TABLE 1

Physical and chemical data of the carriers according to the invention

| Carrier name | A | B |
|---|---|---|
| Content of α-Al$_2$O$_3$ [% by weight] | 99.8 | 99.5 |
| Content of SiO$_2$ [% by weight] | 0.1 | 0.4 |
| Content of HNO$_3$-soluble ions [ppm by weight] | | |
| Al | 300–2000 | 600–2000 |
| Ca | 300–2000 | 500–2000 |
| K | 50–1000 | 50–1000 |
| Na | 50–1000 | 80–1000 |
| BET surface area [m$^2$/g] | 0.60 | 0.60 |
| Water absorption [ml/g] | | |
| cold | 0.45 | 0.46 |
| boiling | 0.50 | 0.51 |
| Bulk density [kg/m$^3$] | 620 | 600 |
| Specific surface area [m$^2$/m$^3$] | 640 | 670 |
| Silver density [kg/m$^3$] | 115 | 115 |

TABLE 2

| Properties of conventional carriers | | | | | | | |
|---|---|---|---|---|---|---|---|
| Carrier name | C | D | E | F | G | H | I |
| Content of α-Al$_2$O$_3$ [% by weight] | 99.8 | 99.5 | 99.8 | 99.8 | 99.8 | 98.5 | 99.6 |
| Content of SiO$_2$ [% by weight] | 0.1 | 0.4 | 0.1 | 0.05 | 0.04 | 1.4 | 0.1 |
| Content of HNO$_3$-soluble ions [ppm by weight] | | | | | | | |
| Al | 250 | 600 | 300 | 100 | 150 | 60 | 130 |
| Ca | 350 | 500 | 400 | 100 | 100 | 10 | 300 |
| K | 20 | 40 | 30 | 5 | 5 | 2 | 10 |
| Na | 30 | 80 | 80 | 60 | 100 | 50 | 20 |
| BET surface area [m$^2$/g] | 0.45 | 0.50 | 0.50 | 0.35 | 0.35 | 0.35 | 0.25 |
| Water absorption [ml/g] | | | | | | | |
| cold | 0.34 | 0.33 | 0.35 | 0.39 | 0.28 | 0.31 | 0.22 |
| boiling | 0.43 | 0.42 | 0.43 | 0.48 | 0.35 | 0.35 | 0.25 |
| Bulk density [kg/m$^3$] | 730 | 730 | 600 | 650 | 810 | 810 | 1050 |
| Specific surface area [m$^2$/m$^3$] | 670 | 670 | 570 | 630 | 630 | 630 | 670 |
| Silver density [kg/m$^3$] | 100 | 100 | 90 | 105 | 110 | 110 | 85 |

TABLE 3

| Results of the experiments according to Use Example 1 | | |
|---|---|---|
| Carrier | Selectivity [%] | Activity [°C.] |
| A | 82.3 | 219 |
| B | 82.2 | 220 |
| C | 81.9 | 222 |
| D | 81.9 | 225 |
| E | 81.5 | 227 |
| F | 81.0 | 221 |
| G | 80.9 | 224 |
| H | 80.1 | 230 |

TABLE 3-continued

| Results of the experiments according to Use Example 1 | | |
|---|---|---|
| Carrier | Selectivity [%] | Activity [°C.] |
| I | 80.0 | 226 |

TABLE 4

| Results of the experiments according to Use Example 2 | | | | |
|---|---|---|---|---|
| Carrier | Selectivity [%] at 35% O$_2$ conversion | Activity [°C.] | Selectivity [%] at 50% O$_2$ conversion | Activity [°C.] |
| after 1 month | | | | |
| A | 82.5 | 196 | 81.5 | 220 |
| B | 82.5 | 197 | 81.3 | 220 |
| C | 82.1 | 200 | 80.4 | 226 |
| F | 81.5 | 200 | 80.0 | 228 |
| I | 81.0 | 204 | 79.5 | 234 |
| after 12 months | | | | |
| A | 81.5 | 200 | 80.4 | 228 |
| B | 81.6 | 205 | 80.4 | 230 |
| C | 80.5 | 210 | 79.0 | 238 |
| F | 80.2 | 208 | 78.4 | 242 |
| I | 79.4 | 213 | 77.0 | 249 |

We claim:

1. A silver catalyst for the direct oxidation of ethylene with oxygen to give ethylene oxide comprising a porous carrier containing at least 99% by weight of α-alumina, from 200 to 2000 ppm of calcium ions, from 200 to 2000 ppm of aluminum ions, at least 50 ppm of potassium ions and at least 50 ppm of sodium ions, said carrier having a BET surface area of from 0.2 to 0.8 m$^2$/g, a pore volume of not less than 0.5 ml/g, the pores being equally accessible to cold and warm water, a bulk density of less than 650 kg/m$^3$, a shape which, in the reactor, provides a geometric surface area of not less than 600 m$^2$/m$^3$, and having applied thereon, as the active component, more than 13% by weight of silver, more than 110 kg of silver being available per m$^3$ of the reactor.

2. A silver catalyst as defined in claim 1, wherein the carrier has a BET surface area of not less than 0.3 m$^2$/g and not more than 0.7 m$^2$/g.

3. A silver catalyst as defined in claim 1, wherein the pore distribution is bimodal, the larger pores accounting for not less than 50% of the total pore volume and having a mean diameter of from 10,000 to 40,000 nm, and the smaller pores having a diameter of from 500 to 2,000 nm.

4. A process for the preparation of a silver catalyst as defined in claim 1, wherein $\alpha$-$Al_2O_3$ is used as the carrier, and the catalytically active material is applied by impregnating the carrier, in one or more stages, with a silver salt solution which contains complex-forming additives and alkali metal salts, and is also heated in one or more stages, not less than 13% by weight of silver being deposited on the catalyst carrier and an amount of silver corresponding to not less than 110 kg per $m^3$ of reactor being achieved.

5. A silver catalyst as defined in claim 1, wherein the carrier contains from 300 to 2000 ppm of Al ions, 300 to 2000 ppm of Ca ions, from 50 to 1000 ppm of K ions and from 50 to 1000 ppm of Na ions.

* * * * *